US012083246B2

(12) United States Patent
Horkay et al.

(10) Patent No.: US 12,083,246 B2
(45) Date of Patent: Sep. 10, 2024

(54) COMPOSITE GELS AND METHODS OF USE THEREOF

(71) Applicant: THE UNITED STATES OF AMERICA, AS REPRESENTED BY THE SECRETARY, DEPARTMENT OF HEALTH AND HUMAN SERVICES, Bethesda, MD (US)

(72) Inventors: Ferenc Horkay, North Potomac, MD (US); Peter Joel Basser, Washington, DC (US)

(73) Assignee: THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 680 days.

(21) Appl. No.: 16/783,494

(22) Filed: Feb. 6, 2020

(65) Prior Publication Data

US 2020/0254144 A1 Aug. 13, 2020

Related U.S. Application Data

(60) Provisional application No. 62/802,885, filed on Feb. 8, 2019.

(51) Int. Cl.
*A61L 27/48* (2006.01)
*A61K 9/06* (2006.01)
*A61K 47/32* (2006.01)
*A61L 27/38* (2006.01)
*C08J 3/075* (2006.01)
*C08J 3/24* (2006.01)
*C08L 29/04* (2006.01)

(52) U.S. Cl.
CPC ............ *A61L 27/48* (2013.01); *A61K 9/06* (2013.01); *A61K 47/32* (2013.01); *A61L 27/3817* (2013.01); *A61L 27/3834* (2013.01); *C08J 3/075* (2013.01); *C08J 3/24* (2013.01); *C08L 29/04* (2013.01); *A61L 2430/00* (2013.01); *C08J 2329/04* (2013.01); *C08J 2433/02* (2013.01)

(58) Field of Classification Search
CPC . A61K 47/32; C08J 3/24; C08L 29/04; A61L 2430/00
See application file for complete search history.

(56) References Cited

U.S. PATENT DOCUMENTS

| | | | |
|---|---|---|---|
| 5,171,775 A | 12/1992 | Graiver et al. | |
| 5,192,326 A | 3/1993 | Bao et al. | |
| 5,752,974 A | 5/1998 | Rhee et al. | |
| 6,060,534 A * | 5/2000 | Ronan | A61L 29/145 523/105 |
| 6,083,522 A | 7/2000 | Chu et al. | |
| 6,231,605 B1 | 5/2001 | Ku | |
| 8,017,139 B2 | 9/2011 | Thomas et al. | |
| 8,491,630 B2 | 7/2013 | Chernomorsky et al. | |
| 8,541,484 B2 | 9/2013 | Choi et al. | |
| 2005/0220882 A1 | 10/2005 | Pritchard et al. | |
| 2007/0005140 A1 | 1/2007 | Kim et al. | |
| 2007/0093907 A1 | 4/2007 | Goupil et al. | |
| 2009/0081275 A1 | 3/2009 | Rolfes et al. | |
| 2015/0225646 A1* | 8/2015 | Li | C08J 3/24 47/65.5 |
| 2016/0038643 A1* | 2/2016 | Detamore | A61L 27/50 514/777 |
| 2018/0221453 A1 | 8/2018 | Muthalagu et al. | |

FOREIGN PATENT DOCUMENTS

WO 2007050744 A2 5/2007
WO 2010045491 A1 4/2010

OTHER PUBLICATIONS

Er-Yuan Chuang et al., "Hydrogels for the Application of Articular Cartilage Tissue Engineering: A Review of Hydrogels" Hindawi: Advances in Materials Science and Engineering, Article ID 4368910, 2018, 13 pages.

* cited by examiner

*Primary Examiner* — Andrew S Rosenthal
(74) *Attorney, Agent, or Firm* — McBee Moore & Vanik IP, LLC

(57) ABSTRACT

A self-reinforcing composite gel includes a solvent, and a plurality of swellable crosslinked polymer particles dispersed in a crosslinked polymer matrix, wherein the crosslinked polymer matrix and the plurality of swellable crosslinked polymer particles are immersed in the solvent, wherein the swellable crosslinked polymer particles absorb more solvent at equilibrium than the matrix polymer, and wherein the plurality of swellable crosslinked polymer particles swell in the solvent and are present in an amount sufficient to maintain or increase the elastic modulus and/or load-bearing ability of the self-reinforcing composite gel, i.e., compared to that of the crosslinked matrix polymer alone, upon swelling in the solvent.

22 Claims, 6 Drawing Sheets

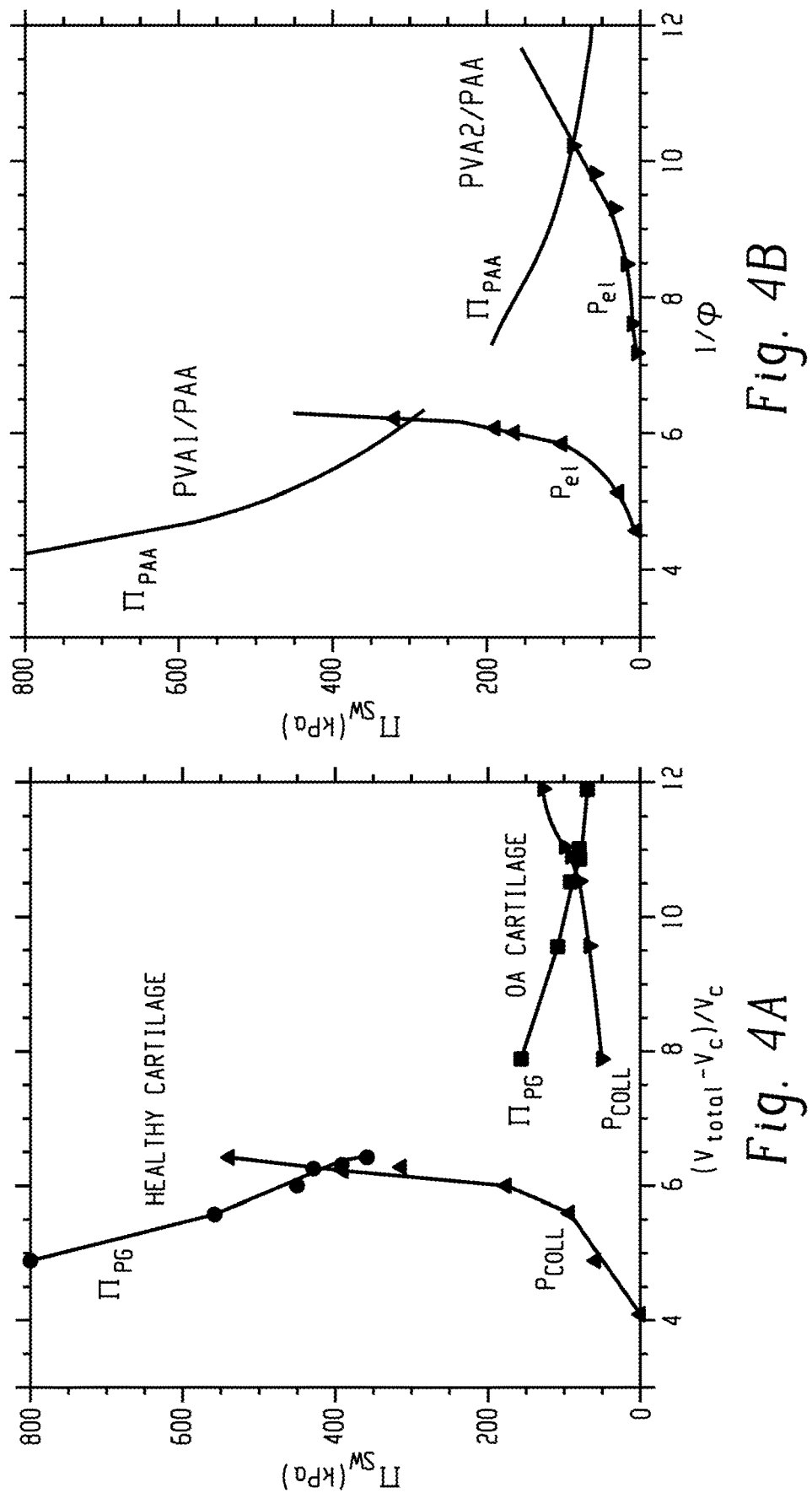

COMPOSITE GELS AND METHODS OF USE THEREOF

CROSS-REFERENCE TO RELATED APPLICATIONS

This application claims priority to U.S. Provisional Application 62/802,885 filed on Feb. 8, 2019, which is incorporated herein by reference in its entirety.

STATEMENT REGARDING FEDERALLY SPONSORED RESEARCH & DEVELOPMENT

This work was supported by the Eunice Kennedy Shriver National Institute of Child Health and Human Development of the National Institutes of Health. The government has certain rights in the invention.

FIELD OF THE DISCLOSURE

The present disclosure is related to composite gel systems, e.g., composite hydrogels. Certain composite hydrogels disclosed herein resemble human cartilage and can be used for cartilage and intervertebral disc repair in addition to non-biological applications.

BACKGROUND

Gel materials, such as hydrogel materials, typically lose mechanical strength as they swell. This property of gels limits their use in both biological (e.g., cartilage repair), and non-biological (e.g., engineering and construction sealing and repair) applications.

Many gel materials have been described for cartilage repair applications. Articular cartilage is a thin connective tissue (2 to 4 millimeters (mm) thick) that covers the ends of the bones at the joints. From a polymer perspective, cartilage is a composite gel-like, load-bearing, and self-lubricating tissue. It primarily contains a fibrous collagen meshwork that encapsulates large, negatively charged (anionic) proteoglycan (PG) polymer assemblies. These PG polyelectrolytes, trapped within the collagen matrix imbibe fluid, and "inflate" the network, whereas the collagen network confines the swelling of the PGs, increasing the stiffness of the tissue matrix as it swells. Under a compressive load, fluid is expelled from the tissue; after unloading it recovers its original shape and volume. The resistance of cartilage to deformation and volume changes defines its load-bearing capacity.

In diseases such as osteoarthritis, this load-bearing ability is reduced due to changes in both the chemical composition and the physical properties of its macromolecular constituents.

What is needed are novel materials with properties similar to human collagen based, particular materials that the functional properties of cartilage, such as its load-bearing ability.

BRIEF SUMMARY

In an aspect, a self-reinforcing composite gel comprises a solvent, and a plurality of swellable crosslinked polymer particles dispersed in a crosslinked polymer matrix, wherein the crosslinked polymer matrix and the plurality of swellable crosslinked polymer particles are immersed in the solvent, wherein the swellable crosslinked polymer particles absorb more solvent at equilibrium than the crosslinked matrix polymer, and wherein the plurality of swellable crosslinked polymer particles swell in the solvent and are present in an amount sufficient to maintain or increase the elastic modulus and/or load-bearing ability of the self-reinforcing composite gel upon swelling in the solvent.

In another aspect, a method of tissue repair comprises administering the self-reinforcing composite gels described herein to the site of tissue repair.

In yet another aspect, a method of tissue engineering or regenerative medicine comprises providing a population of cells in the self-reinforcing composite gels described herein.

In a still further aspect, a method of slow drug release comprises administering to a subject in need thereof the self-reinforcing composite gel described herein comprising the drug.

In a still further aspect, a method of pH-dependent drug release comprises administering to a subject in need thereof the self-reinforcing composite gel described herein comprising the drug, wherein the swellable crosslinked polymer particles are in an unswollen state in the stomach and in a swollen state in the intestine, providing drug release to the intestine.

Also included is a method comprising sealing, repairing, or maintaining an engineered or constructed part with the self-reinforcing composite gels described herein.

In an aspect, a method of making a self-reinforcing composite gel comprises
combining a crosslinkable matrix-forming polymer, a plurality of swellable crosslinked polyelectrolyte polymer particles, an acid, a base or a salt to suppress swelling of the plurality of swellable crosslinked polyelectrolyte polymer particles, a crosslinker, a solvent and optionally a buffer, to provide a first solution;
crosslinking the crosslinkable matrix-forming polymer in the first solution to form a crosslinked matrix polymer;
removing the acid, base or salt and the uncrosslinked matrix-forming polymer to provide a second solution, the second solution comprising the crosslinked matrix polymer and the plurality of swellable crosslinked polyelectrolyte polymer particles; and
freeze-thawing the second solution to provide the self-reinforcing composite gel wherein the plurality of swellable crosslinked polyelectrolyte polymer particles are dispersed in the crosslinked polymer matrix, and wherein the crosslinked polymer matrix and the plurality of swellable crosslinked polymer particles are immersed in the solvent;
wherein the swellable crosslinked polyelectrolyte polymer absorbs more solvent at equilibrium than the matrix polymer, and
wherein the plurality of swellable crosslinked polyelectrolyte polymer particles swell in the solvent and are present in an amount sufficient to increase the elastic modulus and/or load bearing ability of the self-reinforcing composite gel upon swelling.

BRIEF DESCRIPTION OF THE DRAWINGS

FIG. 3B shows $\Pi_{sw}$ versus $1/\varphi$ plots for PVA/PAA composite hydrogels at different pH. The three insets show schematically the structure of the fully swollen composite hydrogels ($\Pi_{sw}=0$). Matrix inflation increases with increasing pH. The dashed circles indicate the size of the freely swollen PAA particles. In the inflated hydrogel, the PAA particles are smaller than the fully swollen particles due to the compressive stress imposed by the PVA matrix.

FIGS. 4A-4B show a comparison between (A) the swelling behavior of cartilage samples and (B) PVA/PAA self-reinforcing composite hydrogels of the present disclosure. The x-axis represents the hydration of the cartilage, where $V_{total}$ is the total tissue volume and $V_C$ is the volume of the collagen. In FIG. 4A $\Pi_{PG}$ is the osmotic pressure of the PG component and $P_{COLL}$ is the tensile stress of the collagen network.

Figure 1A:
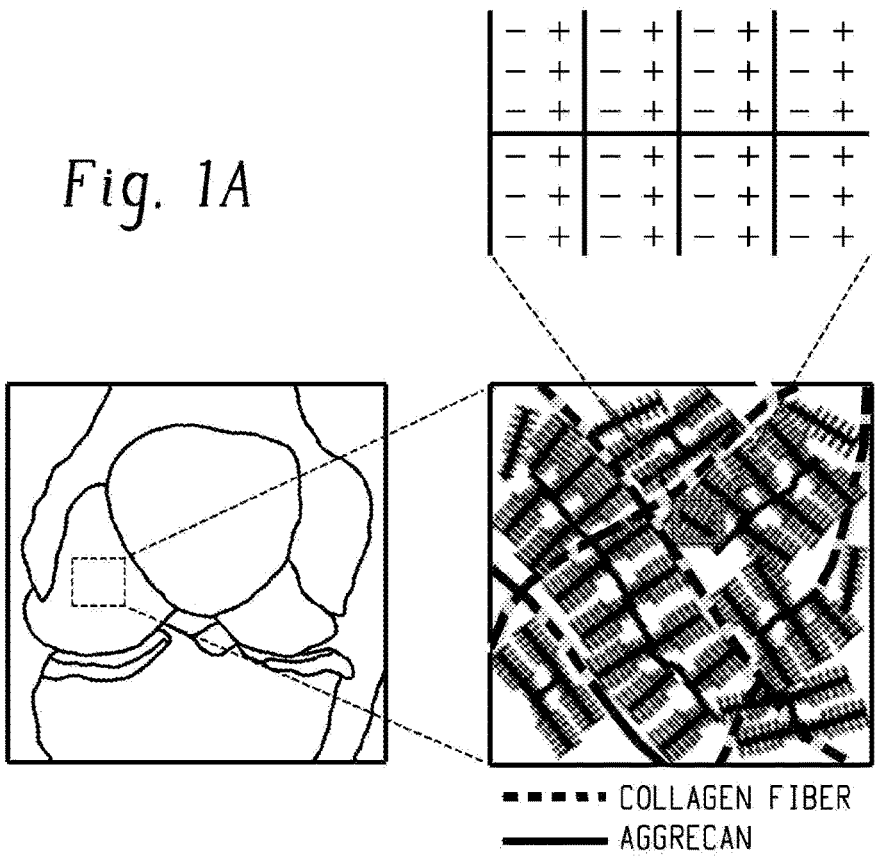
FIGS. 1A-1B show schematic drawings of (A) cartilage ECM and (B) a PVA/PAA composite hydrogel of the present disclosure. In both systems the chains are extended due to the electrostatic repulsive forces between the negatively charged groups. Also shown in (B) are repeat units of PVA and PAA chains; as the pH increases, hydrogen ions are replaced by $Na^+$ ions. Different polymers can be substituted for the PVA/PAA and achieve similar results.

The above-described and other features will be appreciated and understood by those skilled in the art from the following detailed description, drawings, and appended claims.

DETAILED DESCRIPTION

Gels typically exhibit a decrease in mechanical strength (e.g., elastic modulus) upon swelling of the particles. Based on a deeper polymer chemistry and physics-based understanding of the determinants of cartilage and gel properties, the inventors of the present application have unexpectedly found that by selecting a crosslinked polymer matrix and dispersing swellable crosslinked polymer particles such that the swellable crosslinked polymer particles absorb more solvent at equilibrium than the matrix polymer, self-reinforcing composite gels can be made. The individual components (crosslinked polymer matrix and swellable polymer particles) exhibit opposite behavior to the composite, specifically, with increasing swelling the mechanical strength (elastic modulus) of the components (crosslinked polymer matrix and swellable polymer particles) decreases, while the elastic modulus of the composite is unchanged or increases. Such self-reinforcing behavior, increasing the elastic modulus and/or load bearing ability of the self-reinforcing composite gel upon swelling, has not been previously observed in soft composite materials. In this way, one can make a tough polymer composite from soft components.

In an aspect, a self-reinforcing composite gel comprises a solvent, and a plurality of swellable crosslinked polymer particles dispersed in a crosslinked polymer matrix, wherein the crosslinked polymer matrix and the plurality of swellable crosslinked polymer particles are immersed in the solvent. The swellable crosslinked polymer particles absorb more solvent at equilibrium than the crosslinked matrix polymer. As is known in the art, the swellable crosslinked polymer particles and the crosslinked polymer matrix each have an elastic modulus that decreases upon swelling in the solvent. Also, the plurality of swellable crosslinked polymer particles swell in the solvent and are present in an amount sufficient to maintain or increase the elastic modulus and/or load bearing ability of the self-reinforcing composite gel, i.e., compared to that of the crosslinked matrix polymer alone, upon swelling in the solvent.

As used herein, crosslinked generally refers to chemically crosslinked materials, although as understood in the art, chemically crosslinked materials can include a portion of physically crosslinked material, via hydrogen bonding, for example.

Thus, by selecting the crosslinked polymer matrix and the plurality of swellable crosslinked polymer particles such that the swellable crosslinked polymer particles absorb more solvent at equilibrium than the matrix polymer, a self-reinforcing composite gel that has an elastic modulus that stays the same or increases upon swelling in the solvent is formed.

As used herein, the elastic modulus of a polymer or a composite gel is determined by standard ASTM tests known in the art.

In an aspect, the swellable crosslinked polymer particles comprise swellable crosslinked microgel polymer particles. As used herein, swellable crosslinked polymer particles absorb solvent (such as water) and inflate the matrix, that is, the swollen particles exert pressure on the matrix. Exemplary swellable crosslinked polymer particles increase their size upon absorbing solvent (e.g., water). In an aspect, the swellable crosslinked polymer particles are water-swellable polymer particles.

Also as used herein, a crosslinked microgel polymer particle means a polymer particle that forms a gel in response to absorption of solvent (e.g., water).

In another aspect, the swellable crosslinked microgel polymer particles are polyelectrolytes, that is, the polymers contain charged groups. In an aspect, the polyelectrolyte polymer is anionic or cationic.

Exemplary polyelectrolytes for the swellable crosslinked microgel polymer particle include hyaluronic acid, a proteoglycan, dextran particles, crosslinked poly(acrylic acid), crosslinked poly(methacrylic acid), polystyrene sulfonate, their homopolymers, copolymers, block copolymers, or a combination thereof. Polyacrylic acid (PAA) microgels can be synthesized by free-radical copolymerization using the crosslinker N,N'-methylenebis(acrylamide) in aqueous solution.

Non-polyelectrolyte swellable crosslinked microgel polymer particles include a polyethylene glycol, a polyvinyl alcohol, a polyvinylpyrrolidone, a polyacrylamide, or a combination thereof.

Exemplary crosslinked polymer matrix materials include neutral or charged polymers such as collagen. Exemplary materials include cellulose, pectins, chitosan, dextrans, caragemans, alginates, cellulose ethers (such as hydroxypropyl methylcellulose, hydroxypropyl cellulose, hydroxyethyl cellulose, sodium carboxymethylcellulose), hyaluronic acid, albumin, starch, glycosaminoglycans, poly(vinyl alcohols), poly(vinyl alcohol-vinyl acetate polymers), or a combination thereof. For example, poly(vinyl-alcohol) (PVA) gels can be prepared by crosslinking PVA with glutaraldehyde (GDA).

In an aspect, the crosslinked matrix polymer and the swellable crosslinked polymer particles can comprise the same polymer so long as the matrix and particles have different degrees of crosslinking such that the swellable crosslinked polymer particles absorb more solvent at equilibrium than the crosslinked matrix polymer.

In addition to the water-soluble systems described above, the crosslinked matrix polymer and the swellable crosslinked polymer particles can comprise hydrophobic, i.e., non-water soluble polymers. Exemplary hydrophobic polymer include polyvinyl alcohol-polyvinyl acetate copolymers, polydimethylsiloxane (PDMS), polyisoprene (synthetic version of natural rubber), and the like.

In any of the foregoing embodiments, the swellable crosslinked polymer particles have diameters of about 1 micrometer to about 1 mm, whether the particles are swollen or unswollen. Also in any of the foregoing embodiments, the swellable crosslinked polymer particles are present in an amount of 1% v/v to 90% v/v of the total volume of the composite gel.

In an embodiment, the swellable crosslinked polymer particles comprise greater than 10 wt %, 15 wt %, 20 wt %, 25 wt %, 30 wt %, 40 wt % or more of the composite gel, and the crosslinked polymer matrix comprises less than 90 wt %, 85 wt %, 80 wt %, 75 wt %, 70 wt %, 60 wt % of the total weight of polymers in the composite gel.

Exemplary solvents include water, and organic solvents as are known in the art such as dimethyl sulfoxide and tetrahydrofuran. Additional solvents include alcohols (ethyl alcohol, propyl alcohol, isopropyl alcohol, butanol, isobutyl alcohol, glycerol, benzyl alcohol), glycols (ethylene glycol, propylene glycol), organosulfur compounds (dimethyl sulfoxide), higher alkanes (pentadecane, hexadecane, heptadecane, dodecane), hydrocarbons (gasoline, petroleum, n-octane), esters (ethyl acetate, propyl acetate), ketones (methyl ethyl ketone, methyl propyl ketone, diethyl ketone), silicone fluids (cyclosiloxanes, organosiloxane liquids, hexamethyldisoloxane, pentamethylpolysiloxane), and others, and combinations of solvents. Preferably the solvent is water, the polymers are water-soluble, and the gels are composite hydrogels.

The self-reinforcing composite gels described herein are particularly useful for tissue repair, specifically cartilage repair.

In an embodiment, a method of tissue repair comprises administering a self-reinforcing composite gel, e.g., a hydrogel, as described herein to the site of tissue repair. In an aspect, the self-reinforcing composite hydrogel comprises water, and a plurality of swellable crosslinked microgel polyelectrolyte polymer particles dispersed in a crosslinked polymer matrix, wherein the crosslinked polymer matrix and the plurality of swellable crosslinked microgel polyelectrolyte polymer particles are immersed in the water, wherein the swellable crosslinked microgel polyelectrolyte polymer absorbs more water at equilibrium than the matrix polymer, and wherein the plurality of swellable crosslinked microgel polyelectrolyte polymer particles swell in the solvent and are present in an amount sufficient to maintain or increase the elastic modulus and/or load bearing ability of the self-reinforcing composite hydrogel upon swelling in the water. Exemplary sites of tissue repair include a site in need of cartilage repair, a site in need of intervertebral disc repair, breast site in need of an implant, and the like.

In an embodiment, the site of tissue repair is a site of collagen repair. Cartilage extracellular matrix (ECM) is primarily composed of collagens, proteoglycans (PGs), water, and ions. The most abundant class of macromolecules in cartilage ECM is collagen, whose molecules are organized into fiber bundles that form a network at larger length scales, which is inflated by highly swollen PG assemblies enmeshed in the matrix. These PGs exhibit a hierarchical bottlebrush organization. The major PG in cartilage is the bottlebrush-shaped aggrecan. Intracellularly synthesized aggrecan molecules are secreted into the ECM, where they form a secondary bottlebrush with hyaluronic acid (HA) stabilized by a link protein. The osmotic swelling pressure of the aggrecan-HA assemblies inflate the surrounding collagen matrix (FIG. 1A). At swelling equilibrium, the tissue is prestressed, conferring unique mechanical properties on cartilage. At equilibrium, although the total swelling pressure is zero, the collagen matrix is in tension.

In degenerative joint diseases (e.g., osteoarthritis) cartilage structure is progressively damaged. Changes in the stiffness of the collagen matrix and/or loss of PGs strongly affect the biomechanical properties (e.g., load-bearing capacity) of the tissue.

Attempts have been made to describe the mechanical behavior of cartilage in terms of physical models. For example, the cartilage network has been likened to a network of strings that form a tethered fishnet that, when inflated by balloons trapped within the network, can adjust the network tension. This composite material has been shown to support significant loads when the balloons are sufficiently inflated. The extent of network inflation is proportional to (i) the number (concentration) of balloons and (ii) the mesh size of the network. Systems containing large numbers of strongly inflated balloons are much stiffer than those with a small number of weakly inflated balloons.

By exploiting prestress, structures may considerably increase their load-bearing capacity, analogously to reinforced concrete. The tensegrity model as applied to concrete also shares some features with cartilage, having both tensile and compressive elements. The balance of tension and compression elements can stabilize the structure.

Model hydrogels with tunable swelling and mechanical properties have been widely used to mimic various biological tissues, including cartilage. One of the challenges in constructing a biomimetic model of cartilage, however, is to incorporate prestress, which is present even in the absence of external loading, and which plays a critical role in governing the tissue's load-bearing ability.

Figure 1B:
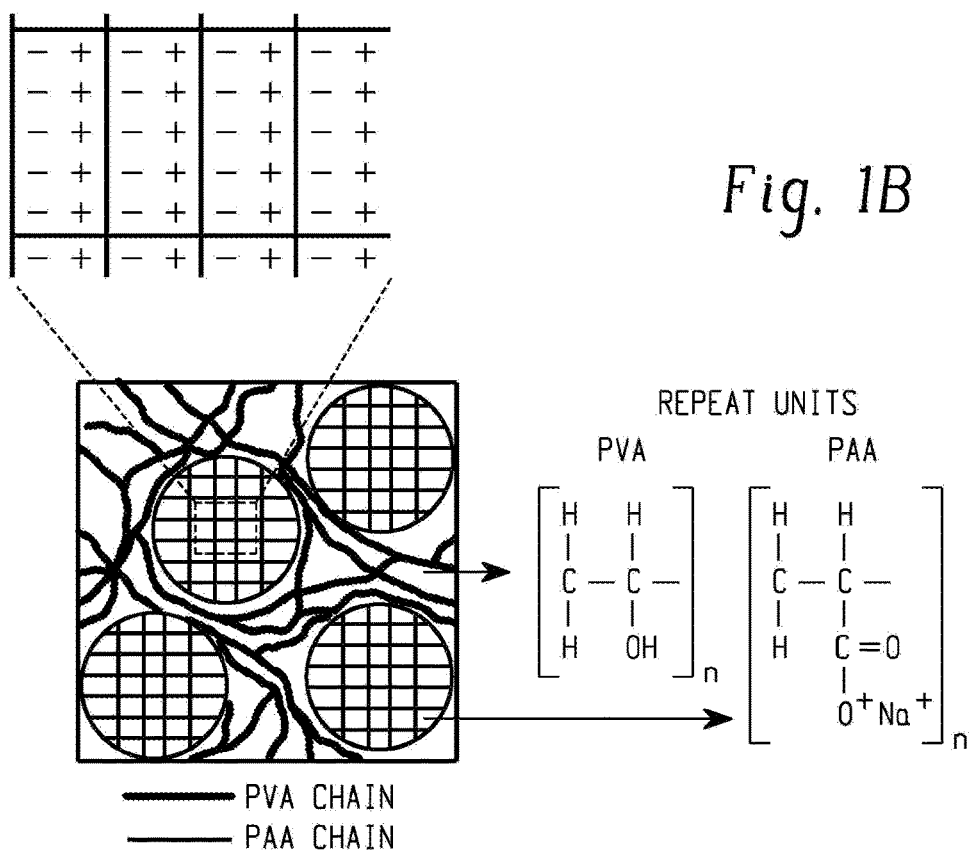

Described herein are self-reinforcing composite gels, e.g., composite hydrogels, based on a quantitative understanding of how network swelling modulates the properties of composite gels that behave similarly to cartilage. In a specific aspect, a prestressed biomimetic composite gel comprises a poly(vinyl alcohol) (PVA) matrix that encapsulates weakly crosslinked poly(acrylic acid) (PAA) microgel particles. PAA is an exemplary polyelectrolyte polymer. In the composite hydrogel, the PVA network corresponds to the collagen matrix, while the PAA particles play the role of the PG polyelectrolyte microgel component (FIG. 1B). The PAA, in equilibrium with pure water (or physiological salt solution), absorbs more water than the PVA and inflates the matrix. The stress of retraction generated in the PVA matrix constrains the swelling of PAA in equilibrium.

In this embodiment, the self-reinforcing composite hydrogels utilize the swelling pressure of PVA and PAA gel networks to create a prestressed tissue model system that mimics the osmotic and mechanical behavior of cartilage, however, the composites disclosed herein are not the same as naturally occurring cartilage. At the preparation condition, for example, both components are stress-free in the PVA/PAA composite hydrogel. As the PAA swells, the PVA network is under increasing tension. At the same time, the PAA component is under compression. Although the unloaded system is in equilibrium, both components are deformed from their original configurations. Described herein is the swelling behavior of the PVA/PAA self-reinforcing composite gels, the prestress in these systems, and a comparison with data reported for healthy and osteoarthritic cartilage in the literature.

Also included are methods of tissue engineering or regenerative medicine using the self-reinforcing composite gels described herein. In another aspect, a method of tissue engineering or regenerative medicine comprises providing a population of cells in a self-reinforcing composite hydrogel, the self-reinforcing composite hydrogel comprising water, and a plurality of swellable crosslinked microgel polyelectrolyte polymer particles dispersed in a crosslinked polymer matrix, wherein the crosslinked polymer matrix and the plurality of swellable crosslinked microgel polyelectrolyte polymer particles are immersed in the water, wherein the swellable crosslinked microgel polyelectrolyte polymer absorbs more water at equilibrium than the matrix polymer, wherein the plurality of swellable crosslinked microgel polyelectrolyte polymer particles swell in the water and are present in an amount sufficient to maintain or increase the elastic modulus and/or load bearing ability of the self-reinforcing composite hydrogel upon swelling in the water. Exemplary cells include chondrocytes, allogenic stem cells, syngenic stem cells, and the like.

Also included are methods of slow drug release using the self-reinforcing composite gels described herein. In yet another embodiment, a method of slow drug release comprises administering to a subject in need thereof a self-reinforcing composite gel comprising the drug, the composite gel comprising a solvent, and a plurality of swellable crosslinked microgel polyelectrolyte polymer particles dispersed in a crosslinked polymer matrix, wherein the crosslinked polymer matrix and the plurality of swellable crosslinked microgel polyelectrolyte polymer particles are immersed in the solvent, wherein the swellable crosslinked microgel polyelectrolyte polymer absorbs more solvent at equilibrium than the matrix polymer, wherein the plurality of swellable crosslinked microgel polyelectrolyte polymer particles swell in the solvent and are present in an amount sufficient to maintain or increase the elastic modulus and/or load bearing ability of the self-reinforcing composite hydrogel upon swelling in the water.

In another aspect, a method of pH-dependent drug release comprises administering to a subject in need thereof the self-reinforcing composite gel described herein comprising the drug, wherein the swellable crosslinked polymer particles are in an unswollen state in the stomach and in a swollen state in the intestine, providing drug release to the intestine. The pH, ionic concentration including ammonium ions and divalent ions such as calcium can regulate release of the drug from the composite gel.

In addition to the biological applications, the self-reinforcing composite gels can be used for various non-biological applications, such as engineering and construction applications. Included herein is a method of sealing, repairing, or maintaining an engineered or constructed part with the self-reinforcing composite gels described herein. One use is in the repair/maintenance of tunnels. The gels described herein can be used to prevent/minimize groundwater infiltration through the walls. For example, in tunnel systems, infiltration of water erodes the wall, and may cause damage in sensitive equipment in the tunnel such as the electrical system. The self-reinforcing composite gels may also be used as sealants in drainage systems. Improved sealing can be achieved if the sealant becomes harder/stronger when the water level in the pipe increases. The composite hydrogels can also be used for repair of damaged sewer pipes. Self-reinforcing polymer composites are ideal materials to repair leaking sewers. The self-reinforcing composite hydrogels can be used as building material, e.g., repairing concrete joints. The polymer composite can be filled with a filler (e.g., Portland cement) making the appearance of the repaired part similar to that of concrete. The composite gels can also be used for underwater application for engineered structures (e.g.; waterproof cables), swimming pools, and the like.

In addition, non-aqueous versions of the composite gels have important applications for sealing of joints of oil pipes or for self-reinforcing o-rings. A non-aqueous self-reinforcing composite gel can be made from, e.g., fumed silica filled crosslinked poly(dimethyl siloxane) containing embedded polyisoprene, polybutadiene or a vulcanized rubber dispersion for this purpose.

Methods of making self-reinforcing composite gels are also included herein. In an embodiment, a method of making a self-reinforcing composite gel comprises combining a crosslinkable matrix-forming polymer, a plurality of swellable crosslinked polyelectrolyte polymer particles, an acid, a base or a salt to suppress swelling of the plurality of swellable crosslinked polyelectrolyte polymer particles, a crosslinker, optionally a buffer, and a solvent to provide a first solution, crosslinking the crosslinkable matrix-forming polymer in the first solution to form a crosslinked matrix polymer, removing the acid, base, or salt and the uncrosslinked matrix-forming polymer to provide a second solution, the second solution comprising the crosslinked matrix polymer and the plurality of swellable crosslinked polyelectrolyte polymer particles, and freeze-thawing the second solution to provide the self-reinforcing composite gel wherein the plurality of swellable crosslinked polyelectrolyte polymer particles are dispersed in the crosslinked polymer matrix, and wherein the crosslinked polymer matrix and the plurality of swellable crosslinked polymer particles are immersed in the solvent, wherein the swellable crosslinked polyelectrolyte polymer absorbs more solvent at equilibrium than the matrix polymer, wherein the plurality of swellable crosslinked polyelectrolyte polymer particles swell in the solvent and are present in an amount sufficient to increase the elastic modulus and/or load bearing ability of the self-reinforcing composite gel upon swelling.

In an aspect, the method further comprises combining the crosslinking of the crosslinkable matrix-forming polymer with freeze thawing to provide partial crystallization of the crosslinked matrix polymer.

The invention is further illustrated by the following non-limiting examples.

EXAMPLES

Methods

Gel preparation: Poly(vinyl-alcohol) (PVA) gels were prepared by crosslinking with glutaraldehyde (GDA) at pH=1.0 in aqueous solutions. For the experiments, fully hydrolyzed and fractionated polymer samples were used ($M_w$, PVA=110 kDa). Crosslinks were introduced at 4% (w/w) polymer concentration; the molar ratio of monomer units to the molecules of crosslinker was 200. After gel formation, the samples were equilibrated with 100 mM NaCl solution to remove HCl and uncrosslinked polymer. Then the gels were dried, reswollen in 100 mM NaCl solution, and exposed to two (PVA1) and eight (PVA2) cycles of freezing for 12 to 14 hours at −20° C. and thawing for 10 hours at 25° C.

The preparation of polyacrylic acid (PAA) gels has been described in the art. Gels were synthesized by free-radical copolymerization from their respective monomers and the crosslinker N,N'-methylenebis(acrylamide) in aqueous solution. Ammonium persulfate was used as an initiator. After gelation, the acrylic acid units were neutralized with NaOH solution. The dry polymer was ground into a powder having an average particle size <10 microns.

PVA/PAA composite hydrogels were prepared by crosslinking PVA in an aqueous solution containing PAA particles. First, the HCl was added to the solution (pH≈1) to suppress the swelling of PAA. Then, the suspension was crosslinked by GDA. The molar ratio of the monomer units to the crosslinker was the same as in the case of the pure PVA gels. The composite gels were treated to the same freeze-thaw process as the PVA gels.

Osmotic stress measurements: Gels were equilibrated with poly(vinyl pyrrolidone) solutions (molecular weight: 29 kDa) of known osmotic pressure. A semipermeable membrane was used to prevent penetration of the polymer into the network. When equilibrium was reached, the polymer concentration in both phases was measured. This procedure yielded the dependence of the osmotic swelling pressure on the polymer concentration for each hydrogel.

Small Angle Neutron Scattering (SANS) Measurements: SANS measurements were made on the NG3 instrument at NIST, Gaithersburg MD. The incident wavelength was 8 Å. The sample-detector distances were 1.2, 4, and 13.1, m corresponding to a wave vector range $0.005 \text{ Å}^{-1}<q<0.1 \text{ Å}^{-1}$. The ambient temperature during the experiments was 25±0.1° C. Gel samples were prepared in $D_2O$ solutions in 2-mm thick sample cells. After azimuthal averaging, corrections for incoherent background, detector response, and cell window scattering were applied.

Example 1: Synthesis of PVA/PAA Composite Hydrogels

PVA is a neutral polymer that is relatively insensitive to changes in the properties or composition of the surrounding solution (e.g., salt concentration, pH). Chemically and/or physically crosslinked PVA gels are widely used in biomedical applications. Many attempts have been made to create PVA gels with mechanical properties (stiffness, etc.) similar to those of cartilage. As described herein, this goal was achieved by combining chemical crosslinking of PVA with partial crystallization induced by freeze thawing. PVA/PAA composite gels were prepared by dispersing PAA microgel particles in a PVA solution (1:1 ratio) prior to PVA crosslinking. The size of the PAA particles was in the range of 5 to 10 μm. Glutaraldehyde was used to crosslink the PVA molecules. The gels were equilibrated with 100 mM NaCl solution. The pH was varied by adding appropriate amounts of 0.1 M NaOH solution. FIG. 1B shows the repeating monomeric units of PVA and PAA chains.

Example 2: Characterization of PVA/PAA Composite Hydrogels

The swelling pressure, $\Pi_{sw}$, of the composite hydrogels was determined by an osmotic stress technique. The composite hydrogel described herein is a novel type of soft matter. It is different from the so-called double-network hydrogels, which consist of two polymer networks, a short-chain and a long-chain network. In a double network, the polymer components are strongly interpenetrated. Double networks are stronger than single components, however upon swelling, the elastic modulus of the double network does not increase. However, in the PVA/PAA composite hydrogels described herein, the two networks are not interpenetrated. Furthermore, small angle neutron scattering (SANS) measurements indicated that the interaction between the matrix polymer and the encapsulated gel particles was negligible. Previous investigations showed the absence of significant interaction between the major polymeric components of cartilage ECM, collagen, and aggrecan.

Figure 2A:
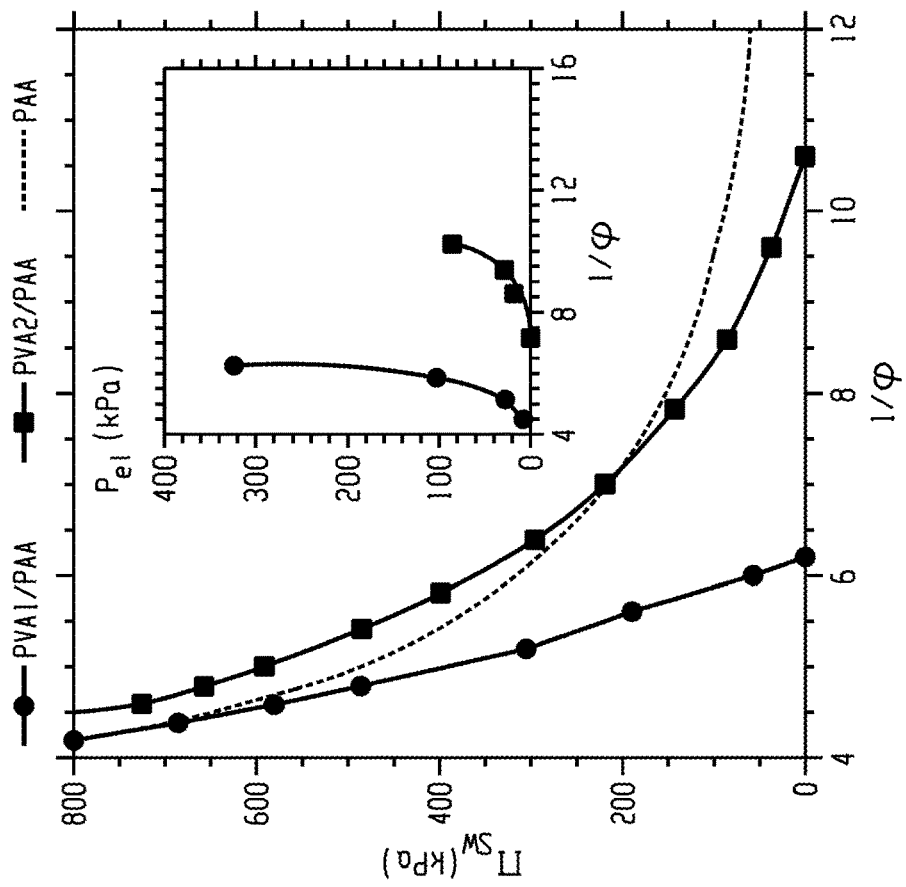
FIGS. 2A-2B show $\Pi_{sw}$ versus $1/\varphi$ plots for (A) PVA and (B) PVA/PAA composite hydrogels. Continuous curves through the data points provide visual guides. The dashed curves show $\Pi_{mix}$ versus $1/\varphi$ for (A) the uncrosslinked PVA and (B) the swelling pressure for the PAA particles enclosed in the PVA matrix. Insets: (A) $\Pi_{el}$ versus $1/\varphi$ plots and (B) $P_{el}$ versus $1/\varphi$ plots.
Figure 2B:
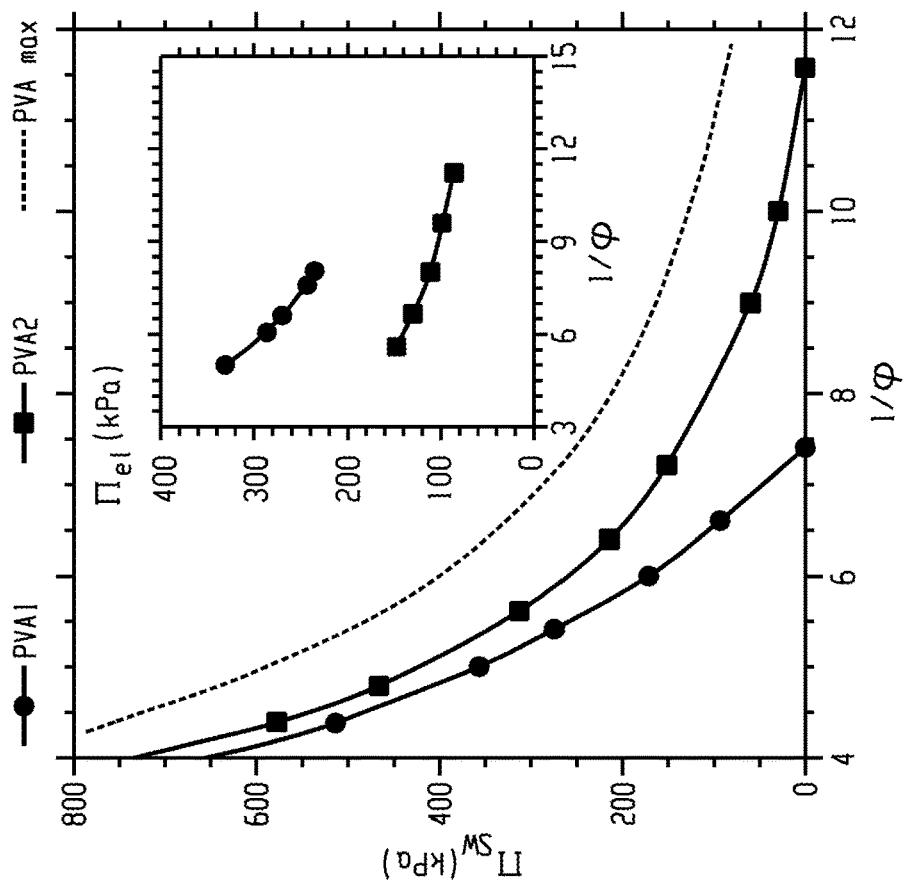

FIGS. 2A-2B shows the variation of $\Pi_{sw}$ as a function of the swelling degree $1/\varphi$ (where $\varphi$ is the volume fraction of the polymer in the swollen network) for PVA (FIG. 2A) and PVA/PAA (FIG. 2B) gels at pH=7. The $\Pi_{sw}$ versus $1/\varphi$ curves for the PVA/PAA composite hydrogels are steeper than for the pure PVA gels. The load-bearing ability of these composite hydrogels is governed by their osmotic compression modulus $K_{os}=\varphi \partial\Pi/\partial\varphi$, which is the measure of the resistance of the hydrogel to a fractional volume change under load. The increase in the slope of the $\Pi_{sw}$ versus $1/\varphi$ plots implies that the load-bearing ability of the composite hydrogels exceeds that of the PVA gels by a factor of approximately two.

While the PVA/PAA composite hydrogel appears to resemble an ordinary filled-polymer network, in filled polymers the filler particles (e.g., fumed silica) form links between the network chains, thus increasing the effective "crosslink density." In the present composite hydrogel, the encapsulated gel particles are not chemically attached to the polymer matrix and, therefore, do not increase the number of contacts between neighboring polymer chains. Consequently, the reinforcing mechanisms in the PVA/PAA hydrogel are predicted to be completely different from that in regular filled-polymer networks.

The driving force of hydrogel swelling is the osmotic pressure of the polymer within the hydrogel, $\Pi_{mix}$, which causes the motion of solvent molecules from a solvent rich region to a region of lower solvent concentration. In the absence of crosslinks, the polymer is completely dissolved (infinite swelling) due to thermodynamic interactions between the polymer and solvent molecules. However, crosslinks prevent infinite swelling because the osmotic pressure of the polymer is counterbalanced by the elastic pressure, $\Pi_{el}$, generated by the crosslinks. In regular prior art polymer hydrogels, the elastic pressure, $\Pi_{el}$, decreases with an increasing degree of swelling reflecting the decrease of the crosslink density. At equilibrium, the solvent flow stops, and the swollen polymer network coexists with the solvent. In other words, $\Pi_{el}$ counteracts $\Pi_{mix}$ and the swelling pressure $\Pi_{sw}$ is zero, as shown in Equation 1

$$\Pi_{sw}=\Pi_{mix}-\Pi_{el}=0 \qquad \text{Eq. (1)}$$

Equation 1 implies that in regular gels, $\Pi_{mix}$ is always greater than $\Pi_{sw}$, i.e., the $\Pi_{sw}$ versus $1/\varphi$ and the $\Pi_{mix}$ versus $1/\varphi$ curves never intersect each other. This behavior is illustrated in the inset of FIG. 2A for both a weakly and a densely crosslinked PVA gel. In both systems, $\Pi_{el}$ decreases monotonically with $1/\varphi$.

FIG. 2B shows that in the self-reinforcing composite hydrogels of the present disclosure, the situation is entirely different. In these systems, the encapsulated PAA gel particles swell and inflate the surrounding PVA matrix. At the concentration where the swelling pressure curves intersect each other, $\Pi_{sw}=\Pi_{PAA}$ (where $\Pi_{PAA}$ is the swelling pressure of the encapsulated PAA gel particles). At higher swelling degrees, the swollen PAA gel particles produce a tensile stress, or prestress, $P_{el}$, and the matrix becomes inflated. The prestress is defined as the difference between the swelling pressure of the enclosed polymer ($\Pi_{PAA}$) and that of the composite gel ($\Pi_{sw}$) as shown in Equation (2).

$$P_{el}=\Pi_{PAA}-\Pi_{sw} \qquad \text{Eq. (2)}$$

The inset in FIG. 2B shows that in the PVA/PAA composite hydrogels, $P_{el}$ steeply increases with increasing swelling degree and reaches a maximum, $P_{el}^{max}$, when the composite hydrogel is fully swollen, i.e., $\Pi_{sw}=0$. At this concentration, the swelling pressure of the PAA is balanced by the prestress developed in the PVA matrix ($\Pi_{PAA}=P_{el}^{max}$). In the absence of external loading, the tensile stress in the PVA is equal to the compressive stress in the PAA and the net stress is equal to zero.

Figure 3A:
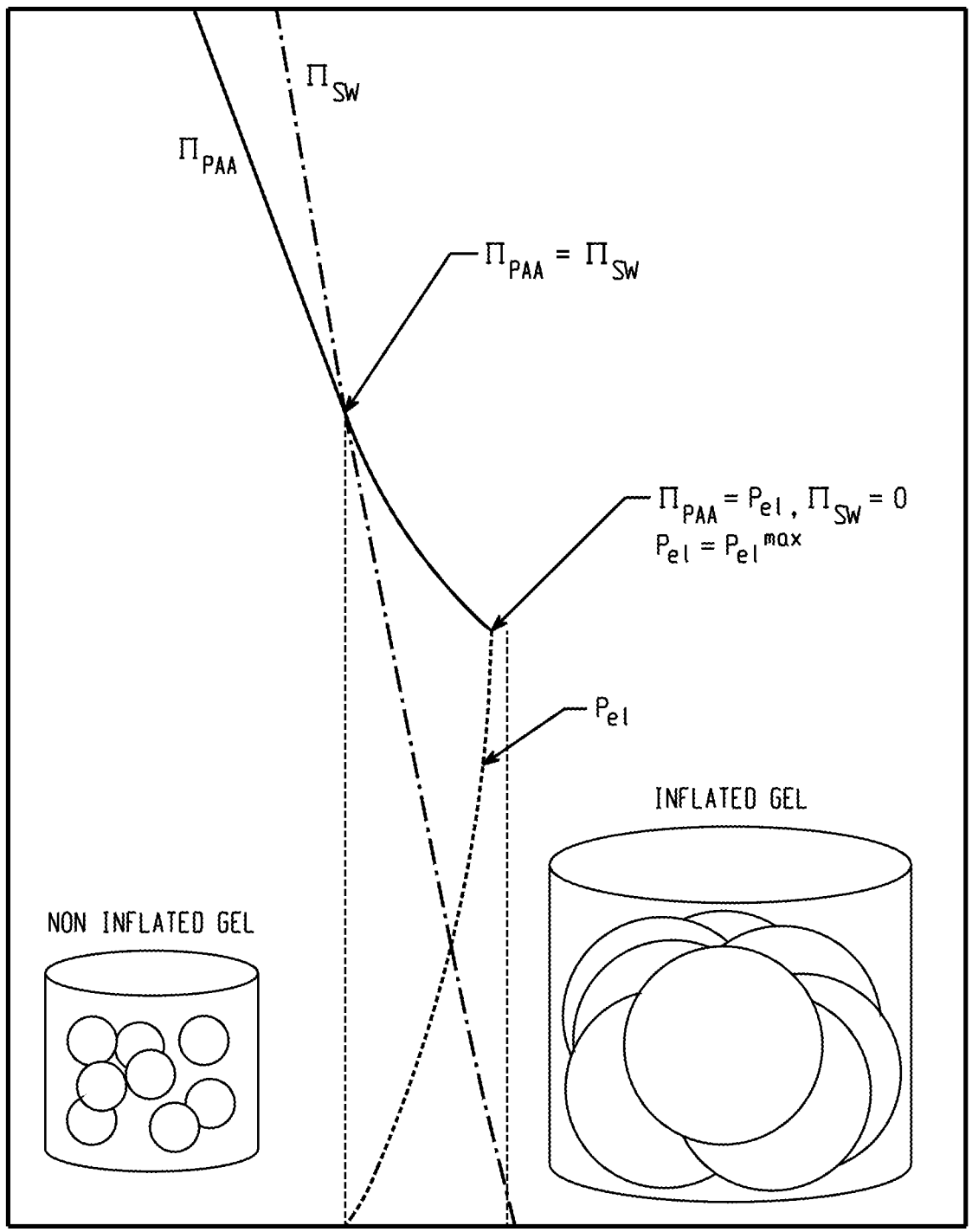
FIGS. 3A-3B show a schematic representation of the osmotic components in a composite hydrogel. At $\Pi_{PAA}=\Pi_{sw}$, the prestress, $P_{el}=0$. In the fully swollen gel, $\Pi_{sw}=0$, and at this point $\Pi_{PAA}=P_{el}=P_{el}^{max}$.

Although formally Eqs. 1 and 2 are similar, there is an important conceptual difference between $P_{el}$ and $\Pi_{el}$. $P_{el}$ increases with increasing swelling degree as shown in FIG. 2B (inset); this behavior is the opposite of the decrease of $\Pi_{el}$ observed in regular gels (inset in FIG. 2A). (The theory of rubber elasticity predicts that in an ideal gel $\Pi_{el} \propto \varphi^{1/3}$). In other words, the high osmotic swelling pressure of the PAA offsets the reduction of $\Pi_{el}$, which implies that the inflated hydrogel operates at an elevated stress level, i.e., the $\Pi_{sw}=0$ condition is shifted upward along the y-axis. Because of the highly nonlinear character of the $\Pi_{sw}$ versus $1/\varphi$ curves, both $\Pi_{sw}$ and the actual swelling degree of the composite hydrogel are reduced. The "strain-hardening" increases with increasing prestress and can be quantified by the osmotic compressional modulus of the hydrogels. We note that the steep increase of $P_{el}$ can be satisfactorily described by the phenomenological Fung hyperelasticity model which is widely used to analyze the load-deformation behavior of diverse biological materials. The situation in the composite gel is illustrated in FIG. 3A.

Figure 3B:
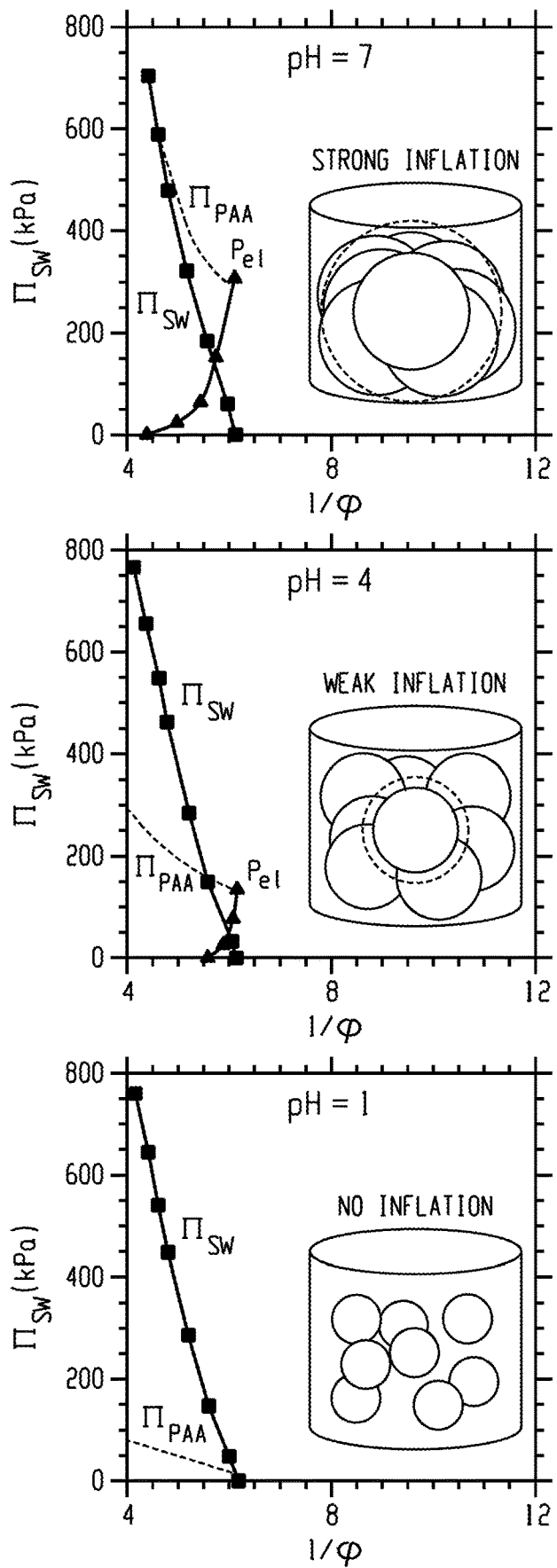

FIG. 3B shows the effect of pH on the inflation of PVA/PAA composite hydrogels at three values of pH (7, 4, and 1). The swelling degree of the PAA component increases with increasing pH and is highest at pH=7. At this pH, the carboxyl groups are dissociated. At pH=4, the swelling of the PAA particles is significantly less than at pH=7, and at pH=1, they hardly swell. At pH=1, the PAA swelling pressure curve lies below the PVA/PAA curve over the entire concentration range, indicating that the carboxyl groups of the PAA are fully protonated and the swelling pressure vanishes. The absence of intersection implies that at pH=1 no prestress is generated in the composite hydrogel. The insets illustrate that the size of the PAA particles in the inflated hydrogel is always smaller than their size when they are freely swollen. The inflated PVA matrix imposes a compressive stress preventing the PAA gel particles from reaching their freely swollen state.

Example 3: Comparison of PVA/PAA Composite Hydrogels to Cartilage

The ultimate test of a biomimetic system is to compare its behavior with its tissue counterpart. For this comparison, high-quality osmotic swelling pressure data previously reported for cartilage was used (FIG. 4A) to investigate the effect of hydration on the tensile stress for normal (healthy) human cartilage samples and for cartilage from an osteoarthritic (OA) joint. In healthy cartilage, the $P_{el}$ versus hydration curves exhibited a steep increase with increasing hydration. By contrast, the swelling pressure curve for the OA specimen was significantly less steep and displaced to higher hydrations. These findings indicate that in OA cartilage the collagen network is weaker. Owing to its high water content, the OA cartilage cannot develop a high PG concentration and, therefore, tissue load-bearing capacity is significantly reduced.

FIG. 4B shows that the osmotic response of the PVA/PAA composite hydrogels of the present disclosure is similar to that of the cartilage tissue. The biomimetic model reproduces both the shape of the cartilage swelling curves and the actual values of the swelling pressure reported for normal and OA tissues.

Load-bearing tissue is ubiquitous in nature. In ECM, the composition and structural organization of its components are critically important because their biochemical and mechanical properties and the complexity of the tissue architecture control the tissue's overall mechanical properties, such as the load-bearing ability.

Example 4: SANS on PVA and PAA Gels And On PVA/PAA Composite Gel

Figure 5:
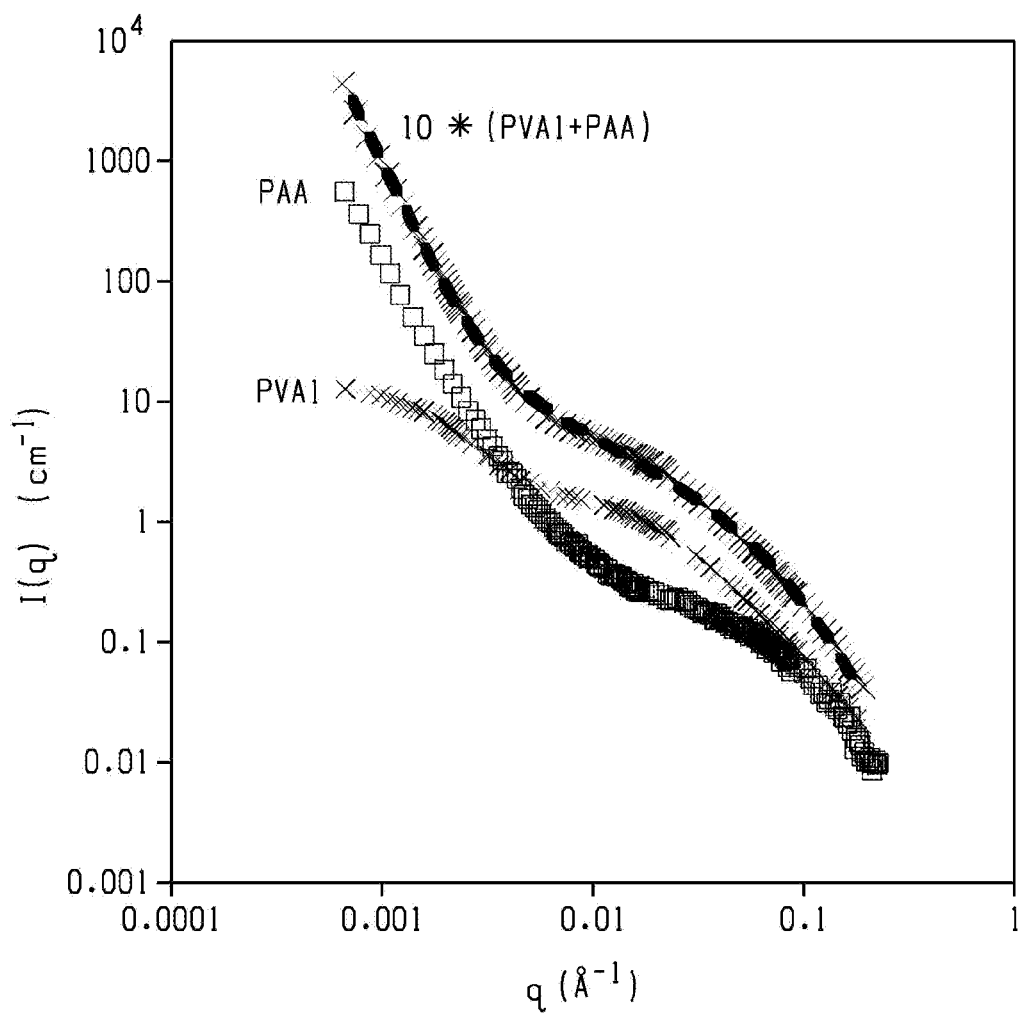
FIG. 5 shows Small Angle Neutron Scattering (SANS) profiles of PVA, PAA, and PVA/PAA composite gels. The intensity of the PVA/PAA curve is multiplied by 10 for clarity. The dashed curve through the PVA1/PAA data points is the sum of the SANS curves of the individual components of the same overall polymer concentration.

Eq. 2 is valid only if there is no interaction between the matrix polymer (PVA) and the enclosed gel particles (PAA). This assumption was validated by making SANS measurements that probe the structure and interactions over a broad range of length scales extending from a few Angstroms to approximately 500 Angstroms. FIG. 5 shows the SANS profiles of the two individual polymers (PVA and PAA) together with that of a PVA1/PAA composite system. The dashed curve through the data points of the composite gel is calculated by assuming additivity of the contributions of the PVA and PAA components. The agreement between the experimental and calculated data indicates that in the PVA/PAA system the interaction between the PVA matrix and the enclosed PAA gel particles is negligible.

Discussion

The main objectives of the field of tissue sciences are to develop quantitative relationships between tissue structure, composition, and its functional properties, identifying and quantifying normal behavior and understanding determinants of pathological deviations from normal behavior. Systematic studies on biomimetic hydrogels could provide vital insights to help understand how factors (e.g., matrix stiffness, charge density) affect the macroscopic mechanical and swelling properties of tissues. This understanding cannot be obtained from measurements made on biological samples because their composition and physical properties cannot be independently and systematically varied as they can be in biomimetic model systems.

Prestress is a key mechanical property of load-bearing biological tissues. Although, its importance has been recognized, its consequences have not yet been fully explored. For example, tissue prestress is clearly a critical factor when designing and engineering a competent cartilage implant or when considering tissue regeneration strategies. Cartilage load-bearing ability is determined by the relative amounts of collagen and PGs and by their structural integrity. The ability of collagen to resist tension confers the shear stiffness of the tissue. PG assemblies inflate the collagen matrix and generate prestress in the collagen network ensuring that the tissue operates in the inflated state (i.e., with increased matrix stiffness) and exhibits enhanced load-bearing properties. High collagen content increases matrix stiffness and, therefore, it is a basic requirement for effective load bearing.

There are various biochemical methods to control the collagen-to-proteoglycan ratio. For example, catabolic enzymes (e.g., chondroitinase, hyaluronidase) deplete PG concentration and increase the tensile properties of cartilage. Suppression of PG synthesis may establish an environment favorable for engineering a deflated matrix. However, reducing the PG concentration also reduces the prestress in the matrix and ultimately decreases the stiffness of the tissue. The composite hydrogels described herein make it possible to systematically investigate the effect of different factors and trade-offs for developing successful tissue engineering strategies that optimize the tissue properties.

Another potential application of the composite hydrogels relates to the treatment of degenerative joint diseases (e.g., OA) by the injection of hyaluronic acid gel particles to reduce osteoarthritis pain. In previous studies, neither the effect of the crosslink density nor the size of the HA particles has been optimized. The load-bearing properties of the composite hydrogels can be maximized by tailoring the crosslink density of the HA gel. Furthermore, the particle size can also be carefully controlled to enable the particles to penetrate the collagen matrix and inflate it.

Described herein is a biomimetic hydrogel model of cartilage comprising a stiff PVA matrix in which PAA microgel particles are embedded. This composite system exhibits entirely different mechanical properties than regular prior art gels. The most remarkable difference is the increase of the elastic pressure with increasing swelling degree. The PAA particles inflate the PVA matrix as the composite hydrogel swells. At equilibrium, the swelling pressure of the PAA is compensated by the tensile stress developed in the PVA and the net "tissue" stress is zero. At pH=7, the PAA particles absorb more liquid than the PVA and inflate the matrix. When the pH is reduced, the swelling pressure of the PAA is diminished due to the increased protonation of the carboxyl groups on the PAA chains, while the swelling of the PVA matrix is practically unchanged because the PVA does not contain ionizable groups and thus will not swell or shrink.

Analysis of the swelling pressure curves of the PVA/PAA composite hydrogels reveals strong similarities with the behavior of cartilage. The biomimetic hydrogels reproduce not only the shape of the cartilage swelling pressure curves but also the numerical values reported for healthy and osteoarthritic cartilage samples.

Example 5: Exemplary Hydrophobic Polymer For The Matrix Of A Self-Reinforcing Composite The PVA matrix was modified by acetylation to produce hydrophobic polyvinyl alcohol-polyvinyl acetate copolymers (PVA-PVAc). This was achieved by placing PVA gels in a mixture of pyridine (50 vol %)-acetic anhydride (40 vol %)-acetic acid(10 vol %). The acetylation reaction was carried out at 95° C. for 12 hours. (To make PVA-PVAc copolymers of different compositions the acetylation process was stopped after 1, 2, and 5 hours.) A fresh mixture was provided each hour. In the last 3 hours the acetic acid was omitted from the fresh mixture in order to shift the equilibrium in the direction of acetate formation. After acetylation the media of the gels were replaced with an organic solvent, e.g., toluene, dimethylsulfoxide.

Example 6: Exemplary Hydrophobic Composite Gel

Polydimethylsiloxane (PDMS) PDMS oil having hydroxylated end groups containing 4% w/w of ethyl triacetoxy silane (ETAS) is stored in an airtight container under dry nitrogen atmosphere. The viscosity of the uncrosslinked oil fraction is 20 P, corresponding to a viscosity average molecular weight of about 40 000 Daltons. Dispersed particles (e.g., crosslinked PDMS) can be blended in the PDMS oil. Gels are prepared by spreading a layer of the mixture with the required thickness on a Teflon® sheet, and allowing atmospheric water to permeate the system. The ETAS molecules, which become attached to the hydroxyl end groups when they are placed in contact, form links with each other, releasing acetic acid. For layers approximately 3 mm thick, the reaction is complete after a 1-2 days. The gel samples are then removed from the Teflon® substrate and allowed to swell in octane, which can be renewed several times in order to remove unreacted polymer. The extractable sol fraction of the gels can be 0.06.

Example 8: Exemplary Hydrophobic Composite Gel

A polyisoprene matrix was made from a poly(cis-isoprene) sample mixed in toluene with different amounts of crosslinking agent (dicumyl peroxide): 0.5, 2, 5 and 10 parts per hundred. The specimens were dried and then baked in an oven at 150° C. for 3 hours. Dispersed particles, e.g., crosslinked PVAc, PDMS, polyisoprene, can be incorporated into the polyisoprene matrix before crosslinking it. It is desirable to use a polyisoprene sample made by anionic polymerization because it results a polymer with a cis-1,4 content of more than 90% as determined by NMR. The high "cis" content significantly enhances strain hardening.

The use of the terms "a" and "an" and "the" and similar referents (especially in the context of the following claims) are to be construed to cover both the singular and the plural, unless otherwise indicated herein or clearly contradicted by context. "Combination thereof" is an open term, optionally allowing the presence of like elements not named. The terms first, second, etc. as used herein do not denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A self-reinforcing composite gel comprising:
a solvent,
   wherein the solvent is water and
a plurality of swellable crosslinked microgel polymer particles dispersed in a crosslinked polymer matrix,
   wherein the swellable crosslinked microgel polymer particles comprise poly(acrylic acid),
   wherein the swellable crosslinked microgel polymer particles range in size from 5 µm to 10 µm;
   wherein the crosslinked polymer matrix comprises a poly(vinyl alcohol),
   wherein the self-reinforcing composite gel is a hydrogel,
   wherein the crosslinked polymer matrix and the plurality of swellable crosslinked microgel polymer particles is immersed in the solvent,
   wherein the swellable crosslinked microgel polymer particles absorb more solvent at equilibrium than the crosslinked matrix polymer,
   wherein the swellable crosslinked microgel polymer particles swell in the solvent and are present in an amount sufficient to maintain or increase the elastic modulus and/or load-bearing ability of the self-reinforcing composite gel upon swelling in the solvent.

2. The self-reinforcing composite gel of claim 1, wherein the swellable crosslinked microgel polymer particles comprise greater than 10 wt % of the self-reinforcing composite gel, and the crosslinked polymer matrix comprises less than 90 wt % of the total weight of polymers in the self-reinforcing composite gel.

3. The self-reinforcing composite gel of claim 1, wherein the swellable crosslinked microgel polymer particles are present in an amount of 1% v/v to 90% v/v of the total volume of the composite gel.

4. A method of tissue repair, comprising administering the self-reinforcing composite gel of claim 1 to a site of tissue repair.

5. The method of claim 4, wherein the solvent comprises water and the swellable crosslinked microgel polymer particles comprise swellable crosslinked microgel polyelectrolyte polymer particles.

6. The method of claim 4, wherein the site of tissue repair is a site in need of cartilage repair, a site in need of intervertebral disc repair, or a breast site in need of an implant.

7. A method of tissue engineering or regenerative medicine, comprising providing a population of cells in the self-reinforcing composite of claim 1.

8. The method of claim 7, wherein the solvent comprises water and the swellable crosslinked microgel polymer particles comprise swellable crosslinked microgel polyelectrolyte polymer particles.

9. The method of claim 7, wherein the cells comprise chondrocytes, allogenic stem cells, or syngenic stem cells.

10. A method of slow drug release, comprising administering to a subject in need thereof the self-reinforcing composite gel of claim 1 comprising a drug.

11. The method of claim 10, wherein the solvent comprises water and the swellable crosslinked microgel polymer particles comprise swellable crosslinked microgel polyelectrolyte polymer particles.

12. A method of pH-dependent drug release, comprising administering to a subject in need thereof the self-reinforcing composite gel of claim 1 comprising a drug, wherein the swellable crosslinked microgel polymer particles are in an unswollen state in the stomach and in a swollen state in the intestine, providing drug release to the intestine.

13. A method comprising sealing, repairing, or maintaining an engineered or constructed part with the self-reinforcing composite gel of claim 1.

14. The method of claim 13, comprising repairing or maintaining a tunnel, sealing a drainage system, repairing a damaged sewer pipe, sealing an oil pipe, or sealing an article underwater.

15. A method of making a self-reinforcing composite gel, comprising
   combining a crosslinkable matrix-forming polymer, a plurality of swellable crosslinked microgel polyelectrolyte polymer particles, an acid, a base or a salt to suppress swelling of the plurality of swellable crosslinked microgel polyelectrolyte polymer particles, a crosslinker, and optionally a buffer, and a solvent to provide a first solution,
   crosslinking the crosslinkable matrix-forming polymer in the first solution to form a crosslinked matrix polymer,
   removing the acid, base or salt and the uncrosslinked matrix-forming polymer to provide a second solution, the second solution comprising the crosslinked matrix polymer and the plurality of swellable crosslinked microgel polyelectrolyte polymer particles, and
   freeze-thawing the second solution to provide the self-reinforcing composite gel
   wherein the plurality of swellable crosslinked microgel polyelectrolyte polymer particles are dispersed in the crosslinked polymer matrix, and wherein the crosslinked polymer matrix and the plurality of swellable crosslinked microgel polymer particles are immersed in the solvent,
   wherein the swellable crosslinked microgel polyelectrolyte polymer absorbs more solvent at equilibrium than the matrix polymer,
   wherein the plurality of swellable crosslinked microgel polyelectrolyte polymer particles swell in the solvent and are present in an amount sufficient to increase the elastic modulus and/or load bearing ability of the self-reinforcing composite gel upon swelling.

16. The method of claim 15, wherein the first and second solutions are aqueous solutions.

17. The method of claim 15, further comprising combining the crosslinking of the crosslinkable matrix-forming polymer with freeze thawing to provide partial crystallization of the crosslinked matrix polymer.

18. The self-reinforcing composite gel of claim 1, wherein the crosslinked polymer matrix and the plurality of swellable crosslinked microgel polymer particles are not chemically attached.

19. The self-reinforcing composite gel of claim 1, wherein the crosslinked polymer matrix is crosslinked through glutaraldehyde (GDA) as a cross-linking agent.

20. The self-reinforcing composite gel of claim 1, wherein the swellable crosslinked microgel polymer particles are crosslinked through N,N'-methylenebis(acrylamide) as a cross-linking agent.

21. The self-reinforcing composite gel of claim 1, wherein:
  the crosslinked polymer matrix is crosslinked through glutaraldehyde (GDA) as a first cross-linking agent; and
  the swellable crosslinked microgel polymer particles are crosslinked through N,N'-methylenebis(acrylamide) as a second cross-linking agent.

22. The self-reinforcing composite gel of claim 1, wherein the crosslinked polymer matrix is at least partially crystalline.

* * * * *